United States Patent [19]

McCollum et al.

[11] 4,017,537

[45] Apr. 12, 1977

[54] NONCATALYZED ALDOL REACTION

[75] Inventors: Anthony W. McCollum; Hugh J. Hagemeyer, Jr., both of Longview, Tex.

[73] Assignee: Eastman Kodak Company, Rochester, N.Y.

[22] Filed: Aug. 25, 1975

[21] Appl. No.: 607,160

[52] U.S. Cl. .............................. 260/494; 260/410.5; 260/410.6; 260/410.9 R; 260/476 R; 260/484 A; 260/491; 260/635 D; 260/635 R

[51] Int. Cl.$^2$ .................. C07C 67/08; C07C 67/44

[58] Field of Search ........... 260/494, 476 R, 484 A, 260/410.9 R, 410.6, 410.5

[56] References Cited

UNITED STATES PATENTS 3,374,267  3/1968  Tan .................................. 260/494

FOREIGN PATENTS OR APPLICATIONS 42-21,687  6/1967  Japan .............................. 260/494

OTHER PUBLICATIONS

Adams, Organic Reactions, 1968, pp. 98–99.

*Primary Examiner*—Vivian Garner
*Attorney, Agent, or Firm*—Donald W. Spurrell; Daniel B. Reece, III

[57] ABSTRACT

The process of carrying out aldol condensations either batch-wise or continuously without catalyst with formaldehyde and another aldehyde in the presence of esterifying acid at a temperature of from about 150° C to about 280° C., with from about 170° C. to about 190° C. being preferred.

5 Claims, No Drawings

NONCATALYZED ALDOL REACTION

This invention concerns a method which may be carried out in a single step, without catalyst, for the aldol condensation of aldehydes with formaldehyde and the subsequent esterification of the aldol product.

It is customary in aldol condensations and subsequent esterifications in the production of beta-acyloxyaldehydes to employ a catalyst. Typical catalysts are the strong acids such as hydrochloric, sulfuric, phosphoric, paratoluenesulfonic, cationic exchange resin, or Lewis acids such as boron trifluoride, aluminum chloride, zinc chloride, and phosphorous trichloride. Such catalysts are expensive, and also corrosive which requires more costly materials of construction. Typically, they must be neutralized before the aldol product is distilled, since the heat required for the distillation in the presence of such catalysts causes loss of yield and promotes the formation of by-products. Further steps are required in separating and disposing of salts of neutralization.

An obeject, therefore, of the present invention is to eliminate the need for catalysts in the preparation of beta-acyloxyaldehydes by aldol condensation and esterification. This and other objects hereinafter appearing have been attained in accordance with the present invention through the process of carrying out the aldol condensation either batchwise or continuously with formaldehyde and another aldehyde in the presence of the esterifying acid at a temperature of from about 150° C. to about 280° C., with from about 170° C. to about 190° C. being preferred.

An example of this general reaction is as follows:

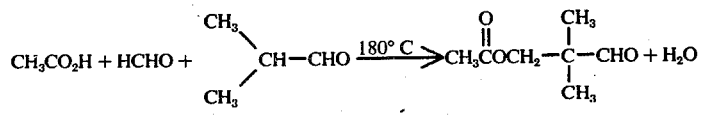

The treatment of a suitable aldehyde containing at least one alpha proton with formaldehyde as formalin, paraformaldehyde, or trioxane in the presence of an organic acid reactant, at a reaction temperature of 150°–280° C. in an autoclave to contain the reactants at autogenous pressure (300–1000 psi) allows the synthesis of aldol products in a single step. Suitable solvents or diluents for the reactants, particularly when they are solids, may be used as expedient for the process. The esterifying acid may be used as the solvent, as can the aldehyde, however, solvents such as saturated hydrocarbons, ethers, and chlorinated hydrocarbons may be selectively employed depending on the solubility characteristics of specific reactants.

The ratios of reactants are not critical although it is preferable to employ enough aldehyde to completely react all of the formaldehyde, for example, 1:1 to 3:1 moles of aldehyde to moles of formaldehyde, and enough acid to esterify all of the hydroxyl radicals formed, for example, 1:1 to 10:1 moles of monocarboxylic acid to —OH radicals. In this regard, formaldehyde is difficult to recover and hence cannot be recycled easily while excess aldehyde and acid can be recovered and recycled readily.

A large variety of aldol products can be prepared by the present process. For example, one or two moles of formaldehyde per mole of aldehyde as shown below may be reacted to provide a polyfunctional molecule useful as chemical intermediates for reduction to polyols, as plasticizers, and for oxidation of the aldehyde to the corresponding acid. Such reactions proceed as follows:

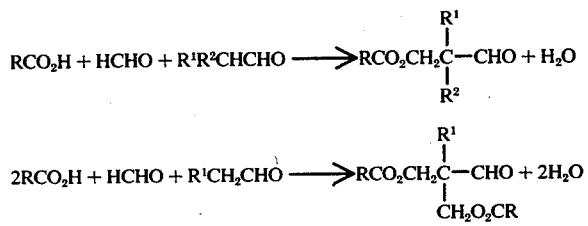

wherein R is selected from alkyl of 1–12 carbons and phenyl, and $R^1$ and $R^2$ each is selected from hydrogen, alkyl of 1–12 carbons, or phenyl.

The invention may be expressed in its broad embodiment as the process for preparing beta-acyloxyaldehydes comprising reacting at a temperature from about 150° C. to about 280° C., formaldehyde, and aldehyde having the formula:

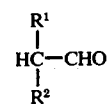

wherein $R^1$ and $R^2$ are each selected from hydrogen, alkyl of 1–12 carbons, and phenyl, and an acid having the formula RCOOH wherein R is alkyl of 1–12 carbons or phenyl.

Depending on the reaction temperature, several coproducts are formed in low yields. In Example 1 below, isobutyraldehyde, formaldehyde, and acetic acid produce the primary product, beta-acetoxypivaldehyde, in 60 percent conversion and yield based on formaldehyde. In addition, acetoxypivalyl acetoxypivalate (1), neopentyl glycol acetate isobutyrate (2), and neopentyl glycol diacetate (3), were isolated. The structures of these coproducts were:

(1)

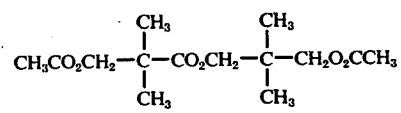

(2)

|         | Reactants |       |     |           | Product $RCO_2CHC-CHO$ with $R^1$ above and $R^2$ below |
|---------|-----------|-------|-----|-----------|---|
|         | $R^1R^2CHCHO$ | | $RCO_2H$ | Reaction | % Conversion |
| Example | $R^1$ | $R^2$ | R | Temp., °C. | (based on formaldehyde) |
| 2  | $C_2H_5$ | $C_2H_5$ | $CH_3$ | 180 | 61 |
| 3  | $C_2H_5$ | $CH_3$   | $CH_3$ | 220 | 52 |
| 4  | $CH_3$   | $CH_3$   | $CH_3$ | 280 | 42 |
| 5  | $CH_3$   | $CH_3$   | Et     | 240 | 44 |
| 6  | $CH_3$   | $CH_3$   | $(CH_3)_2CH$ | 180 | 56 |
| 7  | H        | $CH_3$   | $CH_3$ | 210 | 32 |
| 8  | $C_6H_5$ | H        | $CH_3$ | 220 | 52 |
| 9  | $CH_3$   | $CH_3$   | $C_6H_5$ | 180 | 35 |
| 10 | n-butyl  | $C_2H_5$ | $CH_3$ | 190 | 60 |

|         | Reactants | | Reaction | Product $CH_2O_2CR$ / $R^1C-CHO$ / $CH_2O_2CR$ |
|---------|-----------|---|----------|---|
|         | $R^1CH_2CHO$ | $RCO_2H$ | Reaction | |
| Example | $R^1$ | R | Temp., °C. | %Conversion |
| 11 | n-Propyl | $CH_3$ | 190 | 25 |
| 12 | n-Butyl | $CH(CH_3)_2$ | 210 | 21 |

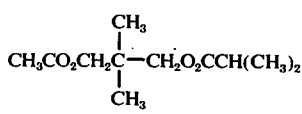

(3) 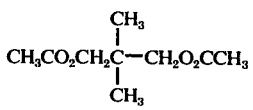

In each case the coproducts are useful as they may be isolated and used as plasticizers, chemical intermediates, transformed to glycols by ester interchange, or reduced to glycols by hydrogenation. The neocarbon skeleton is desirable in glycols which are used in polyesters and plasticizers. The product mixture from Example 1 was hydrogenated and an ester interchange gave a 92 percent yield of neopentyl glycol based on formaldehyde.

The invention will be further illustrated by the following examples although it will be understood that these examples are included merely for purposes of illustration and are not intended to limit the scope of the invention.

EXAMPLE 1

In a one-liter Hastelloy autoclave were charged 512 grams (8.5 moles) acetic acid, 370 grams (5 moles) isobutyraldehyde, and 62 grams (1.84 moles) paraformaldehyde (92 percent). The reaction was run at 180° C. for one hour, cooled to 60° C., and 924 grams of reaction mixture were recovered. Acetic acid and isobutyraldehyde were removed in vacuo to give 156 grams (60 percent conversion based on formaldehyde) of beta-acetoxypivaldehyde, (useful as an intermediate for preparation of pivalolactone in turn useful in preparing polyesters) b.p. 60°/3 mm. In addition, 2.6 grams (0.01 mole) of neopentyl glycol diacetate, 39 grams (0.132 mole) of acetoxypivalyl acetoxypivalate, and 28.5 grams (0.13 mole) of neopentyl glycol acetate isobutyrate were distilled as higher boiling coproducts.

The following examples were run in the same manner as Example 1 varying the aldehyde ($R^1R^2$ CHCHO), acid ($RCO_2H$), or conditions.

The various products obtained above find utility in the preparation of molding and film forming high molecular weight polyesters, particularly copolyesters, prepared from their corresponding beta lactones derived from the oxidation of the product to the acid and the subsequent pyrolization of the acid. This general reaction scheme which is well known to the art may be illustrated with beta-acetoxypivaldehyde as follows:

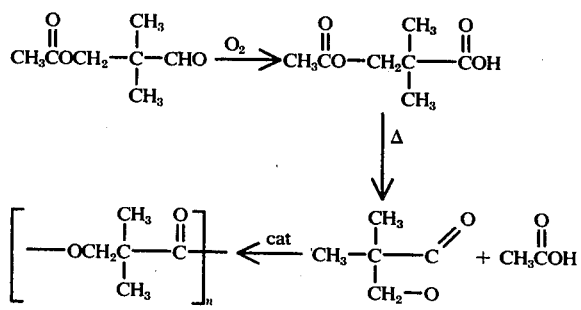

In the case of Examples 11 and 12 above, regulated pyrolysis of the product can remove one of the ester groups while retaining the other to give a polyester having pendant ester groups.

The invention has been described in detail with particular reference to certain preferred embodiments thereof, but it will be understood that variations and modifications can be effected within the spirit and scope of the invention.

We claim:

1. The process for preparing beta-acyloxyaldehydes comprising reacting at a temperature from about 150° C. to about 280° C., formaldehyde, an aldehyde having the formula

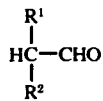

wherein $R^1$ and $R^2$ are each selected from hydrogen, alkyl of 1–12 carbons, and phenyl, and, in the absence of any other acid, an acid having the formula RCOOH wherein R is alkyl of 1–12 carbons or phenyl.

2. The process of claim 1 wherein said aldehyde is in sufficient quantity to react all of the formaldehyde, and said acid is in sufficient quantity to esterify all hydroxy radicals.

3. The process of claim 1 carried out in an autoclave at a pressure between about 300 and 1000 psi.

4. The process of claim 1 wherein the reactants are isobutyraldehyde, paraformaldehyde, and acetic acid, and the principal product is beta-acetoxypivaldehyde.

5. The process of claim 3 wherein the reactants are isobutyraldehyde, formaldehyde and acetic acid wherein said aldehyde is in sufficient quantity to react all of the formaldehyde, and said acid is in sufficient quantity to esterify all hydroxy radicals.

* * * * *